(12) United States Patent
Hirai

(10) Patent No.: US 6,268,736 B1
(45) Date of Patent: *Jul. 31, 2001

(54) DENSITOMETER USING MICROWAVES

(75) Inventor: Renzo Hirai, Tokyo (JP)

(73) Assignee: Kabushiki Kaisha Toshiba, Kawasaki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/215,169

(22) Filed: Dec. 18, 1998

(30) Foreign Application Priority Data

Dec. 22, 1997 (JP) .................................................. 9-352754

(51) Int. Cl.$^7$ .................................................. G01N 22/00
(52) U.S. Cl. .......................................... 324/639; 324/637
(58) Field of Search ..................................... 324/639, 637, 324/640, 642

(56) References Cited

U.S. PATENT DOCUMENTS

| | | | |
|---|---|---|---|
| 5,581,191 | * 12/1996 | Yamaguchi | 324/637 |
| 5,767,685 | * 6/1998 | Walker | 324/640 |
| 5,864,240 | * 1/1999 | Hirai et al. | 324/639 |

FOREIGN PATENT DOCUMENTS

| | | |
|---|---|---|
| 41 17 086 | 11/1992 | (DE) . |
| 0 436 286 | 7/1991 | (EP) . |
| 0 701 118 | 3/1996 | (EP) . |
| WO 95/02815 | 1/1995 | (WO) . |

* cited by examiner

*Primary Examiner*—Safet Metjahic
*Assistant Examiner*—T. R. Sundaram
(74) *Attorney, Agent, or Firm*—Oblon, Spivak, McClelland, Maier & Neustadt, P.C.

(57) ABSTRACT

Microwaves are respectively propagated through a reference fluid and fluid to be measured, both contained in a detection pipe body, and as a result, a first phase lag $\theta 1$ and a second phase lag $\theta 2$ can be determined on the basis of the microwaves by a phase lag measuring circuit. Then, a density computing circuit subtracts the first phase lag $\theta 1$ from the second phase lag $\theta 2$ to determine a phase difference $\Delta\theta$. When computing the density of matter in the fluid on the basis of the phase difference $\Delta\theta$, the density computing circuit performs density computing processing such that a real second phase lag $\theta 2$ satisfies the following equation $$\theta 2 = \theta 2' + N \times 360°$$

where N is the number of rotations, and $\theta 2'$ is an apparent phase lag obtained by the phase lag measuring circuit. Then, if the density does not fall within a checking range defined by upper and lower limit values, a rotation-number checking circuit increases or decreases the number N of rotations such that the density falls within the checking range.

6 Claims, 4 Drawing Sheets

N: NUMBER OF ROTATIONS

DENSITOMETER USING MICROWAVES

BACKGROUND OF THE INVENTION

The present invention relates to a densitometer for measuring the density or concentration of suspended matter contained in fluid, such as the density or concentration of sludge, pulp, and various kinds of soluble matter contained in fluid, and in particular, a densitometer for measuring the density or concentration by using microwaves.

Conventionally, ultrasonic type densitometers and optical type densitometers have been widely used to measure the density or concentration of matter to be measured such as suspended matter contained in fluid. The ultrasonic type densitometer is designed to measure the attenuation of an ultrasonic wave, to thereby determine the density of the matter. The optical type densitometer is designed to measure the attenuation of a transmitted light or the rate at which a scattered light increases, to thereby determine the density of the matter.

The attenuation rate of an ultrasonic wave in air is far greater than in fluid. Accordingly, the attenuation rate of an ultrasonic wave is excessively increased when it is attenuated by bubbles mixing in fluid. Thus, it is considerably great, as compared with the case where an ultrasonic wave is attenuated by the suspended matter in the fluid. In such a manner, the measurement accuracy is greatly influenced by air. As a result, for example, measurement becomes impossible, or the measured density is higher than the actual density.

In order to prevent the influence of bubbles on the measurement, deforming type ultrasonic densitometers have been proposed. In this type of densitometer, fluid to be measured is taken into a pressurizing deforming chamber at a predetermined sampling cycle, and is then pressurized so that bubbles are dissolved in the fluid, and the fluid is measured. However, this method has the following disadvantages:

The mentioned density measurement cannot continuously be performed. Because the mentioned densitometer adapts the sampling method.

The matter to be measured needs to be sampled or pressurized, and thus a mechanical moving section for moving the matter is required, as a result of which the reliability worsens, and the maintenance is troublesome.

In the optical type densitometer, when dirt adheres to an optical window onto which light is emitted or is received, it has an effect on measurement, thus increasing the degree of error in measurement.

In recent years, a densitometer for measuring the density by using microwaves has been put to practical use as a densitometer which is hardly influenced by bubbles or dirt.

FIG. 1 shows the structure of a conventional densitometer using microwaves. Referring to FIG. 1, a microwave transmitting antenna 2 and a microwave receiving antenna 3 are provided on a detection pipe body 1 in which fluid flows, such that they are opposite to each other, and a microwave is emitted from a microwave oscillator 4. A first path is provided on which a microwave is transmitted through a power splitter 5, the transmitting antenna 2, the fluid in the pipe body 1, the receiving antenna 3, and a phase lag measuring circuit 6 in that order. In addition, a second path is provided on which a microwave is transmitted to the phase lag measuring circuit 6 only through the power splitter 5.

The above densitometer compares the phase lag $\theta 2$ of a microwave (represented by reference numeral 102 in FIG. 2) propagated through the detection pipe body 1 filled with the fluid to-be-measured via the first path with respect to a microwave (represented by reference numeral 100 in FIG. 2) transmitted via the second path, with the phase lag $\theta 1$ of a microwave (represented by reference numeral 101 in FIG. 2) transmitted through the detection pipe body 1 filled with a reference fluid such as city water with respect to the microwave (represented by reference numeral 100 in FIG. 2) transmitted via the second path. In this case, the microwave transmitted the detection pipe body 1 filled with the reference fluid is measured under the same condition as the microwave transmitted through the detection pipe body 1 filled with the fluid to be measured. Then, the phase lag $\theta 1$ is subtracted from the phase lag $\theta 2$ to determine the phase difference $\Delta\theta$ ($\Delta\theta=\theta 2-\theta 1$).

The phase difference $\Delta\theta$ is collated with a calibration curve indicating relationships between phase differences $\Delta\theta$ and known density's, to thereby determine the density of the matter contained in fluid to be measured.

To be more specific, the relationship between the density and the phase difference is established to satisfy the following equation:

$$X = C\Delta\theta \quad (1)$$

where X is the density, and C is a coefficient.

In such a manner, in order to determine the density, the densitometer using microwaves does not measure the attenuation of a microwave; it measures the phase difference (the difference between phase lags). Furthermore, in the densitometer, the density measurement is hardly influenced by bubbles or dirt. In other words, it can be correctly performed regardless of the bubbles or dirt, since the window portion on which a microwave is emitted or received does not need to be transparent, but may be dirtied. In addition, the density measurement can be continuously performed.

The phase lags $\theta 1$ and $\theta 2$ are set at optional values in the range of 0° to 360° in accordance with the density, etc. For example, suppose that the phase lag $\theta 1$ corresponding to a reference value (a density of 0) is 300°, and when the density varies by 5%, the phase difference $\Delta\theta$ varies by 100°. Under this supposition, the phase lag $\theta 2$ should be 400°, when fluid to be measured is made to flow into the pipe body 1, and a microwave is transmitted to the fluid.

However, the phase lag $\theta 2$ is apparently 40° since the densitometer indicates the phase lag in the range of 0° to 360°.

More specifically, in the above densitometer (using microwaves), even when the phase lag rapidly varies from a value (e.g., 260° to 360°) close to 360° to a value (e.g., 0 to 100°) close to 0°, it varies actually successively from the value close to 360° to 359°, from 359° to 360° (0°), from 360° (0°) to 1°, and from 1° to the value close to 0°. In this case, when the phase lag varies from 360° (0°) to 1°, it is regarded that it enters the "first rotation".

In this case, as a matter of convenience, the "rotation" is defined as follows: when the phase lag $\theta 2$ is 0° or more and 360° or less (0°≦$\theta 2$≦360°), it is determined as a value of the "zero rotation"; when the phase lag $\theta 2$ is more than 360° and 720° or more (360°<$\theta 2$≦360°), it is determined as a value of the "first rotation"; and when the phase lag $\theta 2$ is more than 720° and 1080° or more (720°<$\theta 2$≦1080°), it is determined as a value of the "second rotation". In other words, when the phase lag $\theta 2$ is (N−1)×360° or more and n×360° or less ((N−1)×360°≦$\theta 2$≦n×360°), it is determined as a value of the "(n−1)-th rotation" (n=an integer), and the phase lag $\theta 1$ is determined as a value of the "zero rotation".

In the above case, it is determined that as shown in FIG. 3, the phase lag θ2 has shifted from the first range of 0° to 360° (which is indicated by "N=0" in FIG. 3) to the second range of 0° to 360° (which is indicated by "N=1" in FIG. 3). Therefore, a correcting arithmetic operation is performed to correct the phase lag θ2. To be more specific, it is performed such that the phase difference Δθ satisfies the following equation (equation 2):

$$\Delta\theta = \theta2' + 360 \times N - \theta1 \quad (2)$$

where θ2' is an apparent phase value, and N is the number of rotations (N=an integer).

In the above case, it is determined that the number N has increased by 1. This concept, as disclosed in Japanese application No. 5-171576, is given under a general process control condition wherein the density of matter to be measured in fluid varies continuously, and does not rapidly vary for a short measurement time period (e.g., five seconds).

In the above densitometer using microwaves, when the fluid in the pipe body 1 is discharged therefrom until the body 1 empties, the density measurement cannot be performed, and needless to say, the density does not continuously vary. In other words, the aforementioned general process control condition is not satisfied. As a result, there is a possibility that the number N of rotations may not be correctly counted. In such a case, the counted number N indicates an excessively high or low value. For example, when the number N=0, if it is mistakenly determined that N=2, the phase difference Δθ is also mistakenly determined in the following manner: the phase lag θ1 is subtracted from the phase lag θ2' to obtain a value, and 720° is added to the value to determine the phase difference Δθ. Actually, the phase difference Δθ should be determined simply by subtracting the phase lag θ1 from the phase lag θ2'. In other words, 720° should not be added. Accordingly, the above mistakenly determined density is higher than the actual density by 720° (360°×2).

Furthermore, if the number N of rotations is still incorrect (for example, it is still determined as 2), the density measurement cannot be correctly performed even if the pipe body is re-filled with fluid after discharge of fluid from the pipe body.

The object of the present invention is to provide a densitometer using microwaves, wherein the density measurement can be correctly performed even if fluid is discharged from a pipe body or fluid is re-filled into the body after discharge of the previously filled fluid therefrom.

BRIEF SUMMARY OF THE INVENTION

In order to solve the above problem, the present invention provides a densitometer which comprises microwave transmitting and receiving systems provided on a detection pipe body or a detection container such that they are located opposite to each other, which determines a first phase lag θ1 of a microwave transmitted through a reference fluid contained in the detection pipe body or detection container, and a second phase lag θ2 of a microwave transmitted through fluid containing matter to be measured in the detection pipe body or detection container, which determines a phase difference Δθ by subtracting the first phase lag θ1 from the second phase lag θ2 (Δθ=θ2−θ1), and then measures the density of the matter on the basis of the phase differences Δθ, the densitometer further comprising:

arithmetic means for determining, in a case where the second phase lag θ2 is 360° or more and 720° or less (360°≦θ2≦720°), or in a case where the second phase lag θ2 is −360° or more and 0° or less (−360°≦θ2≦0°), a real second phase lag θ2 by performing processing so as to satisfy the following equation:

$$\theta2 = \theta2' + N \times 360°$$

where θ2' is an apparent phase lag obtained by transmitting the microwave to and receiving the microwave from the reference fluid, and is 0° or more and 360° or less (0°≦θ2'≦360°), and N is the number of rotations which corresponds to a phase lag, and which is an integer value;

density computing means for computing the density of the matter by using the real second phase lag θ2 determined by the arithmetic means; and rotation-number correcting means for correcting, when the computed density is out of a checking range defined by upper and lower limit values for the density of the matter which are determined in advance, the number N of rotations such that the density computed by the density computing means falls the checking range.

By virtue of the above features, the density measurement can be correctly performed even when the fluid is discharged from the detection pipe body or detection container or fluid is re-filled thereinto after discharge of the previously filled fluid.

Furthermore, a setter for setting the upper and lower limit values for the density may be provided, and the upper and lower limit values may be variable.

The lower limit value of the checking range may be set at a positive value. When the density of matter having a high density is measured, if the lower limit value of the checking range is set at a positive value, the density measurement can be correctly performed.

Moreover, the upper limit value of the checking range may be set at a value which is more than the upper limit value of a density measuring range, and which is equal to or less than a value three times greater than the upper limit value of the density measuring range.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

The embodiment of the present invention will be explained in detail with reference to the accompanying drawings.

Figure 4:
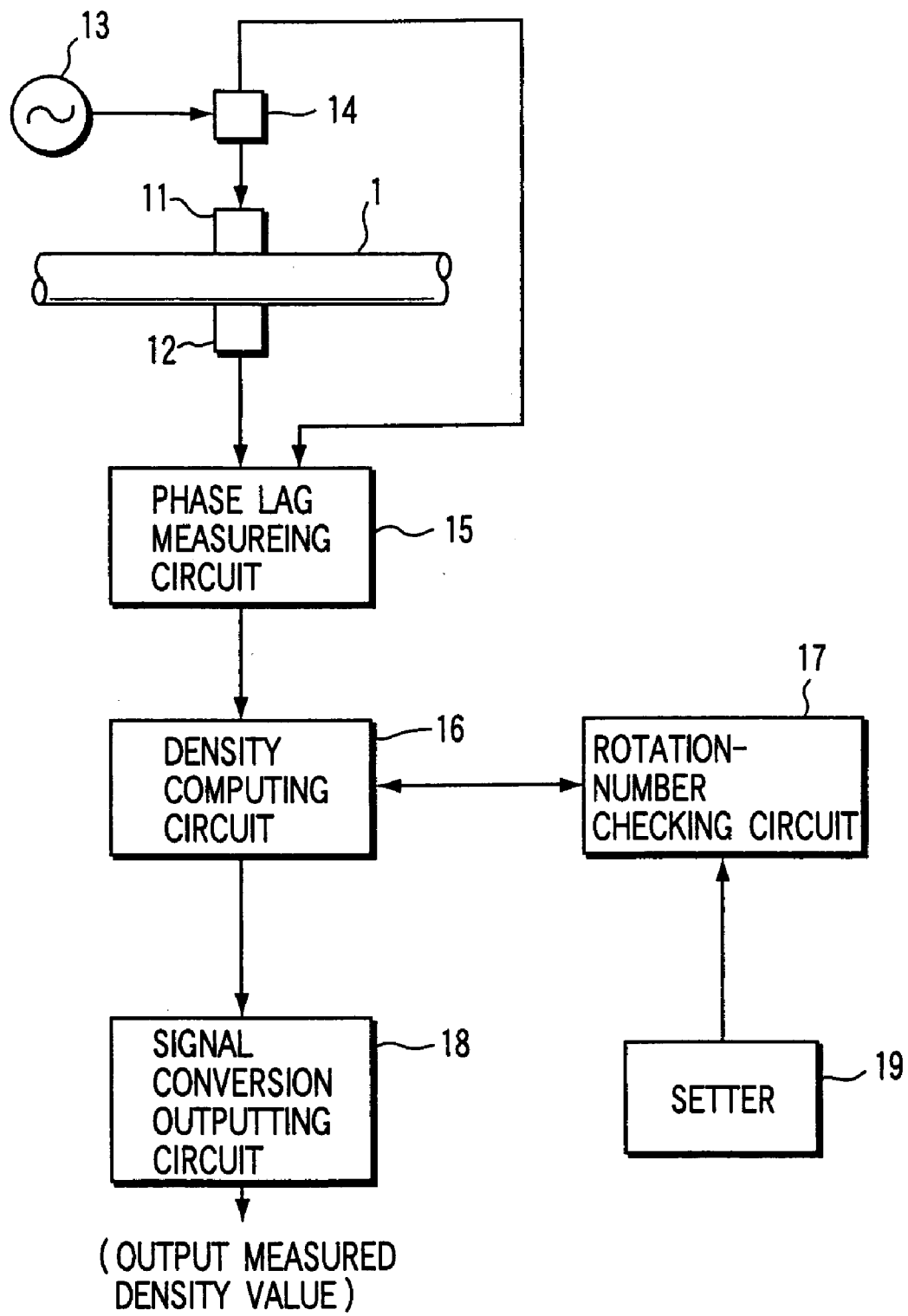
FIG. 4 is a block diagram of a densitometer according to an embodiment of the present invention.

FIG. 4 is a diagrammatic view showing the structure of a densitometer according to the embodiment of the present invention. The densitometer comprises a microwave receiving section and an arithmetic processing section. The microwave receiving section comprises a detection pipe body 1, a microwave receiving antenna 12, a microwave oscillator 13, and a power splitter 14. The arithmetic processing section comprises a phase lag measuring circuit 15, a density computing circuit 16, a rotation-number checking circuit 17 and a signal conversion outputting circuit 18.

As shown in FIG. 4, the microwave transmitting antenna 11 and the microwave receiving antenna 12 are provided on the detection pipe body 1 in which fluid to be measured flows, which contains matter to be measured. The microwave transmitting antenna 11 and the microwave receiving antenna 12 are located opposite to each other. A power splitter 14 is connected to an output side of the microwave oscillator 13. One of the outputting terminals of the power splitter 14 is connected to the microwave transmitting antenna 11, and the other is connected to the phase lag measuring circuit 15. A microwave output from the microwave oscillator 13 is split by the power splitter 14 into microwaves to be respectively transmitted to the microwave transmitting antenna 11 and the phase lag measuring circuit 15.

The microwave transmitting antenna 11 receives the microwave from the power splitter 14, and then emits it to the detection pipe body 1. The microwave is transmitted to the microwave receiving antenna 12 through the fluid in the pipe body 1, and then is send from the receiving antenna 12 to the phase lag measuring circuit 15. The phase lag measuring circuit 15 measures an apparent phase lag $\theta 2'$ of the microwave transmitted from the microwave receiving antenna 12 through the pipe body filled in the fluid, with respect to the microwave directly transmitted from the power splitter 14.

Furthermore, the pipe body is filled in a reference fluid such as city water, and a phase lag $\theta 1$ of the microwave transmitted from the microwave receiving antenna 12 through the pipe body is measured with respect to the microwave directly transmitted from the power splitter 14.

Signals respectively representing the above phase lags $\theta 2'$ and $\theta 1$ are sent to the density computing circuit 16. The computing circuit 16 performs predetermined arithmetic processing to thereby, e.g., determine the phase difference $\Delta\theta$ by subtracting the phase lag $\theta 1$ from the phase lag $\theta 2$ ($\Delta\theta=\theta 2-\theta 1$) and correct the phase lag $\theta 2'$ on the basis of the number N of rotations.

The rotation-number checking circuit 17 and the signal conversion outputting circuit 18 are connected to the density computing circuit 16. The rotation-number checking circuit 17 checks the validity of the number N of rotations on the basis of a result of the above arithmetic processing. The signal conversion outputting circuit 18 outputs the result of the arithmetic processing as data representing a measured density value. A setter 19 is connected to the rotation-number checking circuit 17. It is designed to set an initial value (e.g., N=0) of the number N of rotations and upper and lower limit values for use in checking processing of the rotation-number checking circuit 17.

Figure 1:
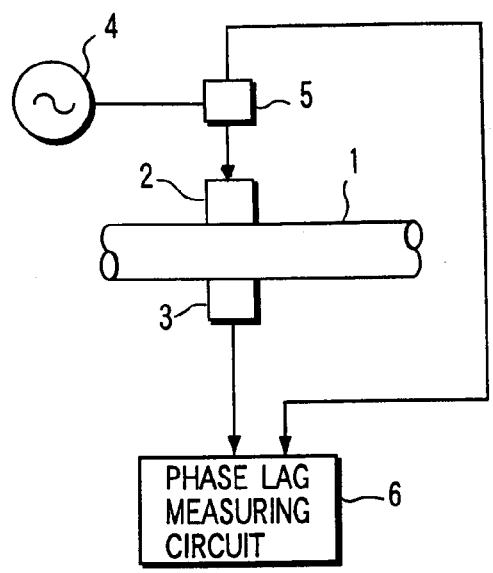
FIG. 1 is a block diagram for showing the structure of a conventional densitometer using microwaves.
Figure 2:
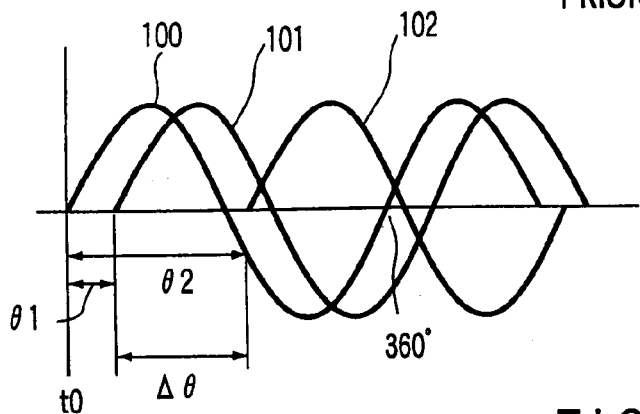
FIG. 2 is a waveform view for illustrating a phase lag of a microwave transmitted through a reference fluid and a phase lag of a microwave transmitted through fluid to be measured.
Figure 3:
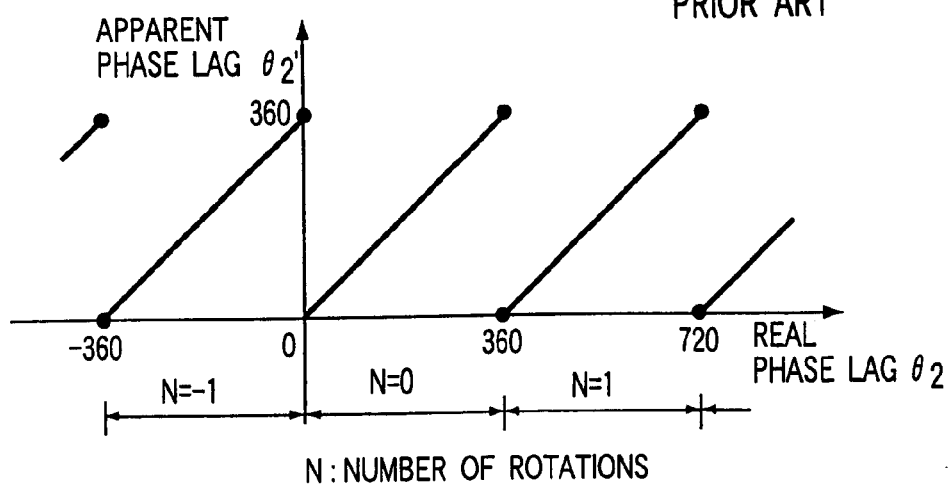
FIG. 3 is a view for illustrating an apparent phase lag and a real phase lag.
Figure 5:
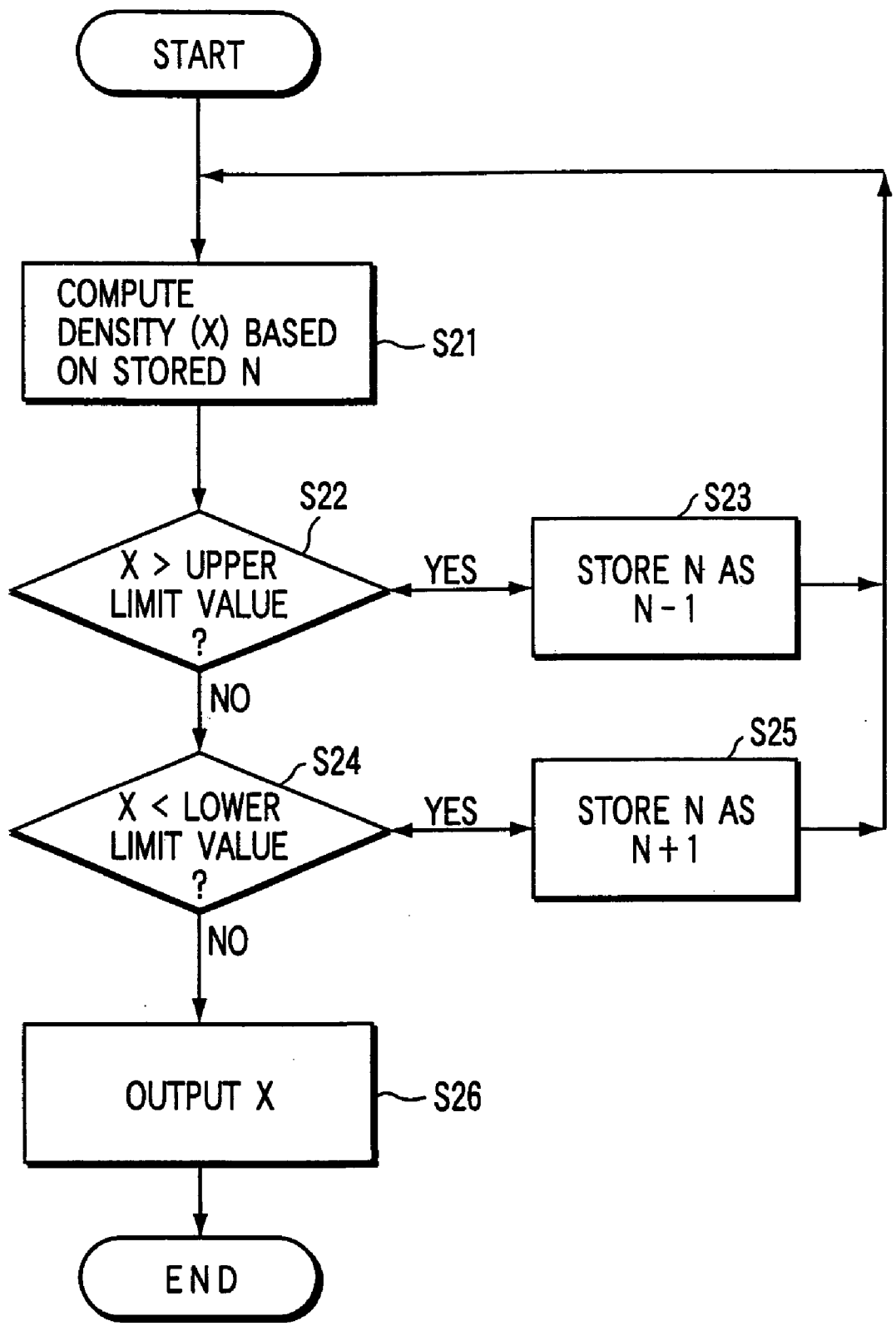
FIG. 5 is a flow chart showing the procedure of density computing processing of the present invention.
Figure 6A:
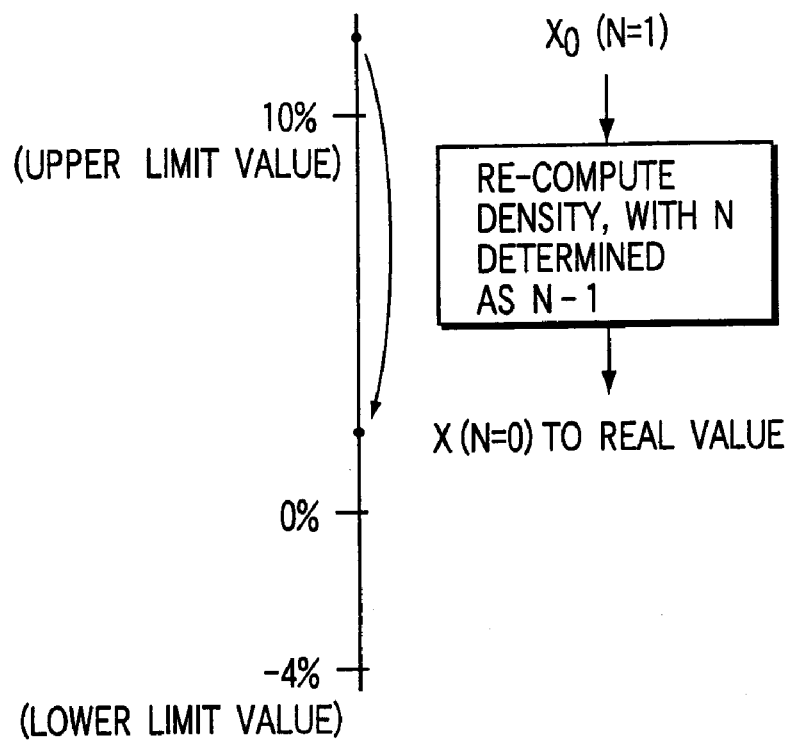
FIG. 6A is a view for illustrating processing which is performed when the density determined by density computing processing is more than an upper limit value.
Figure 6B:
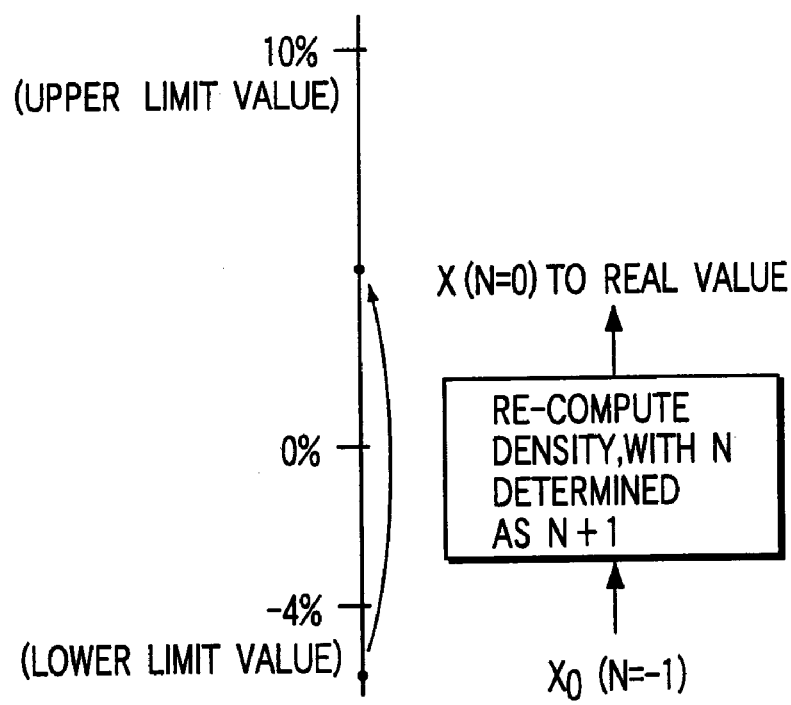
FIG. 6B is a view for illustrating processing which is performed when the density determined by the density computing processing is less than a lower limit value.

Densitometer computing processing and checking processing of the number N of rotations will be explained with reference to FIGS. 3, 5 (flowchart) and 6A and 6B. FIG. 6A is a view for illustrating processing performed when the density is more than the upper limit value, and FIG. 6B is a view for illustrating processing which is performed when the density is less than the lower limit value.

When the density computing circuit 16 performs a density computation, a real phase value is determined from the equation 2 by using the number N stored in the rotation-number checking circuit 17, and further the density X is determined from the equation 1 (step S21). The determined density X is input as data to the rotation-number checking circuit 17. The checking circuit 17 compares the density X with the upper limit value determined in advance as stated above (step S22). When the density X exceeds the upper limit value (See FIG. 6A), the checking circuit 17 determines that the number N of rotations is too large, obtains a value by subtracting 1 from the number N, and stores the value as data (step S23). Then, the density computing circuit 16 performs the arithmetic processing by using the value, thereby to determine a corrected density X (step S21).

On the other hand, when the density X does not exceed the upper limit value, it is compared with the lower limit value determined in advance, by the rotation-number checking circuit 17 (step S24). When it is less than the lower limit value (see FIG. 6B), the checking circuit 17 determines that the number N is too small, obtains a value by adding 1 to the number N, and stores the value as data (step S25). Then, the density computing circuit 16 performs the arithmetic processing by using the value, thereby to determine a corrected density X (step S21).

When the corrected density X falls within a range defined by the upper and lower limit values, a signal representing the density X is output from the signal conversion outputting circuit 18. In contrast, if it does not fall within the range, the above processing is repeated until the corrected density X falls within the range.

The above upper and lower limit values for use in checking will be explained as follows:

For example, as the upper limit value, a density value is adopted, which is, e.g., one-half greater than the upper limit value of the measuring range of the densitometer. In principle, the upper limit value is set at a positive value which is more than the upper limit value of the measuring range of the densitometer. On the other hand, in an actual densitometer, the upper limit value should be set at a positive value which is more than the upper limit value of the above measuring range, and which is equal to or more than a value three times greater than the upper limit value of the measuring range.

The lower limit value for use in checking is set at a negative density value (e.g., 4%) which is actually out of the bounds of possibility.

Those upper and lower limit values may be programmed as predetermined fixed values, or may be set at predetermined values by the setter 19.

By virtue of the above features, the density measurement can be correctly performed, even if the fluid in the pipe body is discharged therefrom, or fluid is re-filled into the pipe body after discharge of the previously filled fluid from the pipe body.

According to the above explanation for the embodiment, the upper limit value for use in checking is a multiple of the upper limit value of the measuring range set in the densitometer. However, it may be a fixed value.

Furthermore, according to the above explanation, the lower limit value for use in checking is a negative density value. However, it may be variable and a positive density value. In particular, when a fluid having a high density is measured, the lower limit value may be set at a positive density value, e.g., 10%, and the upper limit value may be set at, e.g., 20%.

Moreover, the upper and lower limit values may be varied externally by a remote operation.

As explained above, according to the densitometer of the present invention, the density measurement can be correctly performed, even if the fluid in the detection pipe body is discharge therefrom or the detection pipe body is re-filled with fluid after discharge of the previously filled fluid.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A densitometer comprising:

a microwave transmitting/receiving section for transmitting microwaves to and receiving the microwaves from a reference fluid and fluid to be measured which contains matter to be measured; and an arithmetic processing section for determining a first phase lag $\theta 1$ of the microwave received from the reference fluid by the microwave transmitting/receiving section, for determining a second phase lag $\theta 2$ of the microwave received from the fluid to be measured by the microwave transmitting/receiving section, for determining a phase difference $\Delta\theta$ by subtracting the first phase lag $\theta 1$ from the second phase lag $\theta 2$, and for determining a density of the matter in the fluid to be measured on the basis of the phase difference $\Delta\theta$, wherein the arithmetic processing section comprises:

arithmetic means for determining, in any one of cases where the second phase lag $\theta 2$ is 360° or more and 720° or less, and where the second phase lag $\theta 2$ is −360° or more and 0° or less, a real second phase lag $\theta 2$ by performing processing so as to satisfy the following equation:

$$\theta 2 = \theta 2' + N \times 360°$$

where $\theta 2'$ is an apparent phase lag obtained by transmitting the microwave to and receiving the microwave from the reference fluid, and is 0° or more and 360° or less, and N is the number of rotations which corresponds to a phase lag, and which is an integer value;

density computing means for determining a phase difference $\Delta\theta$ by subtracting the first phase lag $\theta 1$ from the real second phase lag $\theta 2$ determined by the arithmetic means, and computing the density of the matter contained in the fluid on the basis of the phase difference $\Delta\theta$ determined by the density computing means; and rotation-number correcting means for correcting, when the computed density is out of a checking range defined by upper and lower limit values for the density of the matter which are determined in advance, the number N of rotations such that the density computed by the density computing means falls within the checking range, comprising, a checking mechanism configured to determine if each density computed by the density computing means is within said range, a change mechanism configured to vary the number N of rotations, when it is determined that the computed density is outside said range, according to whether the density is determined to be above or below said range and to apply a varied number N to the arithmetic means so that said arithmetic means and said density computing means produce a recomputed density based on the varied number N, and said checking mechanism and change mechanism acting to vary the number N iteratively until the density computed by the density computing means is within said range.

2. The densitometer according to claim 1, which further comprises a setter for setting the upper and lower limit values for the density at desired values, respectively.

3. The densitometer according to one of claims 1 and 2, wherein the lower limit value is a positive value.

4. The densitometer according to one of claims 1 to 3, wherein the upper limit value is a positive value which is more than an upper limit value of a range of density measurement.

5. The densitometer according to claim 1, wherein the microwave transmitting/receiving section comprises:

a detection pipe body in which the reference fluid and the fluid to be measured containing the matter to be measured flow;

a microwave oscillator for oscillating the microwave;

a power splitter for splitting an output of the microwave oscillator into outputs;

a microwave transmitting antenna, attached to the detection pipe body, for receiving a microwave which is one of the outputs obtained by the power splitter, and transmitting the received microwave to the fluid to be measured and the reference fluid in the detection pipe body; and a microwave receiving antenna, attached to the detection pipe body, for receiving the microwave transmitted from the microwave transmitting antenna.

6. The densitometer according to claim 1, wherein the arithmetic processing section collates the phase difference $\Delta\theta$ determined by the density computing means with calibration curve-data prepared in advance, to thereby compute the density of the matter to be measured contained in the fluid to be measured.

* * * * *